US012702767B2

(12) United States Patent
Campitelli et al.

(10) Patent No.: US 12,702,767 B2
(45) **Date of Patent: *Aug. 11, 2026**

(54) INHALER SYSTEM WITH SINGLE PLANE PIERCING ELEMENT

(71) Applicant: PHILIP MORRIS PRODUCTS, S.A., Neuchâtel (CH)

(72) Inventors: Gennaro Campitelli, Neuchâtel (CH); Onur Dayioglu, Neuchâtel (CH)

(73) Assignee: Philip Morris Products S.A., Neuchatel (CH)

( * ) Notice: Subject to any disclaimer, the term of this patent is extended or adjusted under 35 U.S.C. 154(b) by 602 days.

This patent is subject to a terminal disclaimer.

(21) Appl. No.: 18/038,893

(22) PCT Filed: Dec. 9, 2021

(86) PCT No.: PCT/IB2021/061519

§ 371 (c)(1),
(2) Date: May 25, 2023

(87) PCT Pub. No.: WO2022/123488

PCT Pub. Date: Jun. 16, 2022

(65) Prior Publication Data

US 2024/0017026 A1 Jan. 18, 2024

(30) Foreign Application Priority Data

Dec. 11, 2020 (EP) .................................... 20213329

(51) Int. Cl.
*A61M 15/00* (2006.01)
*A61M 15/06* (2006.01)

(52) U.S. Cl.
CPC .... *A61M 15/0035* (2014.02); *A61M 15/0041* (2014.02); *A61M 15/06* (2013.01); *A61M 2202/064* (2013.01); *A61M 2206/16* (2013.01)

(58) Field of Classification Search
CPC ............ A61M 15/003; A61M 15/0035; A61M 15/0038; A61M 15/004; A61M 15/0041;
(Continued)

(56) References Cited

U.S. PATENT DOCUMENTS 3,888,253 A * 6/1975 Watt .................. A61M 15/0041 128/203.15
2010/0108062 A1* 5/2010 Ganem ............ A61M 15/0028 128/203.21

(Continued)

FOREIGN PATENT DOCUMENTS

JP 2006-508699 A 3/2006
JP 2011-505905 A 3/2011

(Continued)

OTHER PUBLICATIONS

Japanese Office Action for JP 2023-526988 issued by the Japanese Patent Office on Sep. 29, 2025; 9 pgs. including English translation.

(Continued)

*Primary Examiner* — Joseph D. Boecker
(74) *Attorney, Agent, or Firm* — Mueting Raasch Group

(57) ABSTRACT

An inhaler system includes a housing defining a housing cavity, a sleeve extending along a sleeve longitudinal axis and positioned within the housing cavity, a capsule is contained within the sleeve, and a piercing element comprising only a single shaft extending from a fixed end to a tip along a piercing element longitudinal axis. The piercing element longitudinal axis being parallel with the sleeve longitudinal axis. The piercing element having a piercing element diameter in a range from 0.5 to 0.9 mm. The single piercing element tip having only a single cutting plane and defining a cutting plane angle between the longitudinal axis (Continued)

of the piercing element and the single cutting plane. The cutting plane angle being in a range from about 25 degrees and about 35 degrees.

19 Claims, 7 Drawing Sheets

(58) Field of Classification Search
CPC . A61M 15/06; A61M 2202/064; A24F 40/05; A24F 40/20
See application file for complete search history.

(56) References Cited

U.S. PATENT DOCUMENTS

| | | | | |
|---|---|---|---|---|
| 2011/0277752 A1 | 11/2011 | Cheu et al. | | |
| 2016/0151589 A1 | 6/2016 | Ohrt et al. | | |
| 2017/0135397 A1 | 5/2017 | Buehler et al. | | |
| 2020/0275710 A1* | 9/2020 | Waller | .................... | A24F 42/60 |
| 2024/0091468 A1* | 3/2024 | Dayioglu | ................ | A24F 42/20 |

FOREIGN PATENT DOCUMENTS

| | | | | | |
|---|---|---|---|---|---|
| JP | 2015-536765 | A | 12/2015 | | |
| WO | WO 2003/080163 | A1 | 10/2003 | | |
| WO | WO 2009/075794 | A1 | 6/2009 | | |
| WO | WO 2014/089018 | A2 | 6/2014 | | |
| WO | WO 2018/007886 | A1 | 1/2018 | | |
| WO | WO 2019/159123 | A1 | 8/2019 | | |
| WO | WO 2020/178715 | A1 | 9/2020 | | |
| WO | WO-2020178714 | A1 * | 9/2020 | ............. | A24F 13/08 |

OTHER PUBLICATIONS

European Search Report for EP 20213329.4 issued by the European Patent Office on Jun. 2, 2021; 8 pgs.
International Search Report and Written Opinion for PCT/IB2021/061519, issued by the European Patent Office on Mar. 11, 2022; 13 pgs.
Marple et al., "Next generation pharmaceutical impactor (a new impactor for pharmaceutical inhaler testing). Part I: Design," *Journal of Aerosol Medicine*, 2003; 16(3):283-99.
Marple et al., "Next generation pharmaceutical impactor (a new impactor for pharmaceutical inhaler testing). Part II: Archival calibration," *Journal of Aerosol Medicine*, 2003; 16(3):301-324.

* cited by examiner

INHALER SYSTEM WITH SINGLE PLANE PIERCING ELEMENT

This application is the § 371 U.S. National Stage of International Application No. PCT/IB2021/061519, filed 9 Dec. 2021, which claims the benefit of European Application No. 20213329.4, filed 11 Dec. 2020, the disclosures of which are incorporated herein by reference.

The present invention related to an inhaler system that includes a single plane piercing element. The piercing element provides a comfortable capsule activation and uniform dry particle delivery over at least five inhalations.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose or capsule load in a single breath.

Inhaler articles may retain capsules containing dry powder. These capsules may be activated by piercing an aperture though the capsule wall with a piercing element. A user then puffs (draws or inhales) from the consumable mouthpiece side. This action forces air flow through the dry powder inhaler.

Activating the dry powder capsule requires piercing the capsule to form an aperture. Dry powder particles then may exit the capsule through the aperture during inhalation and consumption of the dry powder particles by entraining the dry particles in the inhalation air flow to the consumer. Forming a reliable open aperture on the capsule hemispherical end has proven to be difficult. Piercing element are known to provide non-uniform apertures. The aperture may also tend to reclose once the piercing element is withdrawn from the capsule further leading to non-uniform apertures. These non-uniform apertures result in a non-uniform release of particles from the capsule or hinder particle release from the capsule altogether. This leads to unpredictable and variable dry powder delivery to the consumer.

It is desirable to provide an inhaler system that reliably pierces the capsule to form a uniform single stable aperture. It is desirable to provide an inhaler system that reliably pierces the capsule with a simple design. It is desirable to provide an inhaler system that reliably pierces the capsule and provides predictable and uniform dry powder delivery to the user over a multitude of inhalations. It is desirable to provide an inhaler system that comfortably pierces or activates a capsule containing dry powder particles.

According to an aspect of the present invention, there is provided an inhaler system comprising a housing defining a housing cavity, a sleeve extending along a sleeve longitudinal axis and positioned within the housing cavity, a capsule contained within the sleeve having a capsule longitudinal axis, and a piercing element comprising only a single shaft extending from a fixed end to a tip along a piercing element longitudinal axis. The piercing element longitudinal axis is parallel with the sleeve longitudinal axis. The piercing element has a piercing element diameter in a range from 0.5 to 0.9 mm. The single piercing element tip has only a single cutting plane and defines a cutting plane angle between the longitudinal axis of the piercing element and the single cutting plane. The cutting plane angle is in a range from about 25 degrees and about 35 degrees. The sleeve is movable within the housing cavity between a first position and a second position. Only a single aperture is formed in the capsule when the sleeve is moved from the first position to the second position.

Applicant has discovered utilizing a single piercing element having a single cutting plane with a cutting angle in a range from about 25 degrees and about 35 degrees coupled with a piercing element diameter in a range from 0.5 to 0.9 mm, advantageously results in reliable and repeatable activation of the capsule which provides a uniform or constant dose or release of particles over at least 5 inhalations of the inhaler system. In addition, this combination of piercing element features advantageously provides a comfortable piercing or activation force experienced by the user. This combination of piercing element features also advantageously provides a robust and simple mechanical design that is simple to assemble.

According to an aspect of the present invention, there is provided an inhaler system comprising a housing defining a housing cavity, a sleeve extending along a sleeve longitudinal axis and positioned within the housing cavity, a capsule is contained within the sleeve having a capsule longitudinal axis, and a piercing element comprising only a single shaft extending from a fixed end to a tip along a piercing element longitudinal axis. The piercing element may be solid. The piercing element may be hollow. The piercing element longitudinal axis is parallel with and offset from the sleeve longitudinal axis. The piercing element has a piercing element diameter in a range from 0.5 to 0.9 mm. The single piercing element tip has only a single cutting plane and defining a cutting plane angle between the longitudinal axis of the piercing element and the single cutting plane. The cutting plane angle is in a range from about 25 degrees and about 35 degrees. The sleeve is movable within the housing cavity between a first position and a second position. Only a single aperture is formed in the capsule when the sleeve is moved from the first position to the second position.

Inhaler systems that utilize a single piercing element to pierce a capsule place this single piercing element coincident with a central longitudinal axis of the device or capsule cavity so that the piercing element strikes the capsule at the central axis of the capsule. It is expected that this configuration would provide a balanced piercing force onto the capsule and avoid a bending moment on the piercing element or the capsule during activation of the capsule.

Applicant has discovered that placing the single piercing element parallel with but offset from the longitudinal axis of the inhaler device or capsule cavity, improves the quality and reliability of the aperture formed in the capsule hemispherical end by the offset piercing element. Specifically, when this single offset piercing element starts cutting on a surface closer to the central longitudinal axis of the inhaler device (along the hemispherical surface of the capsule endcap) to a surface further away from the initial cut point, a hinge of capsule material is formed on the portion forming the apertures perimeter that is furthest from the initial cut point. This specific orientation of the piercing element cutting plane produces a stable open aperture as compared to any other orientation of this piercing element cutting plane.

Advantageously, providing a single offset piercing element forms a repeatably reliable single open aperture in the capsule. The single offset piercing element is a simple mechanical configuration. The single offset piercing element is relatively easy to assembly into an inhaler article holder. The single offset piercing element provides predictably improved uniform dosing over a multitude of inhalations.

This disclosure is directed to a holder for an inhaler article, referred to as an “inhaler article holder”. The inhaler article holder includes a single offset piercing element. The inhaler article holder is configured to receive a consumable inhaler article, activate the capsule within the inhaler article by piercing the capsule, and induce swirling inhalation airflow into an inhaler article during consumption. The inhaler article holder and an inhaler article may form an inhaler system to which this disclosure is directed.

The inhaler article holder described herein may be combined with an inhaler article containing a capsule. The inhaler article may be used to activate the inhaler article by piercing the capsule, providing reliable activation of the capsule by puncturing the capsule with the piercing element of the inhaler article holder. Particles may be released from the capsule upon drawing or creating an airflow around the pierced capsule. The inhaler system thus delivers the dry powder particles to a consumer. The inhaler article holder is separate from the inhaler article, but the consumer utilizes both the inhaler article and the inhaler article holder while consuming the dry powder particles released within the inhaler article. A plurality of these inhaler articles may be combined with an inhaler article holder to form a system or kit. A single inhaler article holder may be utilized on 10 or more, or 25 or more, or 50 or more, or 100 or more, inhaler articles to activate (puncture or pierce) a capsule contained within each inhaler article and provide reliable activation. The inhaler article may optionally provide a visual indication (marking), for each inhaler article of the activation of the inhaler article.

The inhaler article has an airflow path. Airflow is introduced into the inhaler article by an inhalation (or puff) from a user. The inhaler article holder creates swirling inhalation airflow. This swirling inhalation airflow is introduced to the inhaler article. The distal end or upstream-most end of the inhaler article includes an open aperture that defines an open central passage of the open tubular element configured to receive swirling inhalation airflow.

The swirling inhalation airflow then continues downstream into the capsule cavity and induces rotation of a capsule in the capsule cavity. The activated capsule then releases a dose of particles into the swirling inhalation airflow downstream through the mouthpiece to the consumer. Thus, the swirling inhalation airflow is created upstream from the inhaler article and swirling inhalation airflow enters the distal end or upstream-most end of the inhaler article.

An inhaler article comprises an elongated tubular body extending along an inhaler longitudinal axis from a mouthpiece end to a distal end. The mouthpiece end is the proximal end, or the downstream end. The distal end is the upstream end. A capsule cavity is defined within the body bounded downstream by a filter element and bounded upstream by an open tubular element defining a central passage. Prior to insertion into an inhaler article holder, the distal end of the inhaler article may be closed. After insertion into an inhaler article holder, the distal end of the inhaler article may be open. The distal end of the inhaler article may interact with complimentary structures in the inhaler article holder so that, upon introducing the inhaler article into the inhaler article holder, the distal end of the inhaler article may open. When introduced into the inhaler article holder, the distal end of the inhaler article has a central passage which forms an open air-inlet aperture extending from the distal end of the body to the capsule cavity. A capsule is disposed within the capsule cavity, the central passage may have a smaller diameter then the capsule. Thus, the capsule may not pass through the central passage and is retained within the capsule cavity.

The inhaler article holder includes a housing comprising a housing cavity for receiving an inhaler article and a sleeve configured to retain an inhaler article within the housing cavity. The housing cavity is defined by a single housing opening that extends into the housing to a closed end along a housing longitudinal axis. The single housing opening is configured to receive the inhaler article.

The sleeve is contained within the housing cavity and is movable along the housing longitudinal axis between a first position and a second position. The sleeve may be slidable along the housing longitudinal axis between a first position and a second position. In the first position the sleeve is located adjacent to the single housing opening. In the second position the sleeve is further away from the single housing opening a lateral distance along the longitudinal axis.

The sleeve extends from an open end to a closed end (or restricted end) and defines a cylindrical lumen along a longitudinal axis of the sleeve. The open end of the sleeve aligns with the single housing opening.

The sleeve closed end includes an airflow element and an aperture to allow the piercing element to pass through the closed end and extend into the sleeve lumen. The airflow element includes one or more inhalation air inlets that provide airflow communication from the annular space around the sleeve into the sleeve cylindrical lumen. This airflow element is configured to induce rotating or swirling inhalation airflow into the sleeve cylindrical lumen and directly into the inhaler article capsule cavity. This swirling or rotational inhalation airflow may be transmitted into an inhaler article to rotate a capsule and release dry powder contained within the capsule.

The airflow element of the sleeve includes a tubular element having a central passage in fluid communication with the sleeve cavity. The airflow element has at least one air inlet allowing inhalation air to enter into the central passage. The at least one air inlet extends in a direction that is tangential to the central passage to generate the swirling or rotational inhalation airflow.

The airflow element of the sleeve includes a tubular element having a central passage in fluid communication with the sleeve cavity. The airflow element has at least two air inlets allowing inhalation air to enter into the central passage. The at least two air inlets extend in a direction that is tangential to the central passage to generate the swirling or rotational inhalation airflow.

The airflow element of the sleeve includes a tubular element having a central passage in fluid communication with the sleeve cavity. The airflow element has at least three air inlets allowing inhalation air to enter into the central passage. The at least three air inlets extend in a direction that is tangential to the central passage to generate the swirling or rotational inhalation airflow.

The airflow element may include an aperture to receive and allow the piercing element to pass through the airflow element.

Inhalation air may enter the inhaler article holder through the open aperture receiving the inhaler article and travel into the housing cavity along the length of the inhaler article to the airflow element at the sleeve closed end. Alternatively, inhalation air may enter the inhaler article holder through air inlets through the housing surface.

The inhaler article holder includes a piercing element fixed to and extending from a housing inner surface of the cavity. The piercing element includes a single solid shaft extending from a fixed end to a tip along the piercing element longitudinal axis. The piercing element is configured to extend through the closed end of the sleeve and into the sleeve cavity along a longitudinal axis of the housing. The piercing element contacts and pierces the capsule of a received inhaler article once the sleeve moves from the first position to the second position. Moving the sleeve from the second position to the first position removes the piercing element from the capsule and exposes an aperture in the capsule that allows dry particles contained within the capsule to be released from the capsule as inhalation air rotates the capsule.

The inhaler system or inhaler article holder piercing element described herein is a single piercing element that has a single cutting plane, a diameter in a range from 0.5 to 0.9 mm, and a cutting plane angle in a range from about 25 degrees and about 35 degrees. Preferably the piercing element shaft defines a solid cylinder with the single cutting plane defined on the free end tip of the piecing element. The piercing element may also be hollow with a single cutting plane defined on the free end tip of the piercing element. The inhaler system has less than two piercing elements. The inhaler system forms less than two apertures in the capsule containing dry powder particles.

The inhaler system or inhaler article holder piercing element described herein is a single piercing element that has a single cutting plane, a diameter in a range from 0.5 to 0.9 mm, and a cutting plane angle in a range from about 25 degrees and about 35 degrees, and the single piercing element may be offset from the longitudinal axis of the inhaler article holder, or offset from the inhaler article holder movable sleeve receiving an inhaler article, or offset from the capsule cavity containing a capsule, or offset from the longitudinal axis of the capsule or axis of rotation of the capsule when the capsule spins during inhalation and consumption of the dry particles released from an activated capsule. The inhaler system has less than two piercing elements. The inhaler system forms less than two apertures in the capsule containing dry powder particles.

The inhaler system or inhaler article holder piercing element described herein is a single piercing element that strikes and pierces a hemispherical endcap of the capsule, contained within the capsule cavity of the inhaler device. The single piercing element strikes and pierces a hemispherical endcap of the capsule. The single piercing element may strike and pierce the hemispherical endcap of the capsule offset from the central longitudinal axis of the capsule and the central longitudinal axis of the sleeve and central longitudinal axis of the capsule cavity. The single piercing element may strike and pierce the hemispherical endcap of the capsule not at the central longitudinal axis of the capsule.

The piercing element shaft has a shaft diameter. The shaft diameter is in a range from about 0.5 mm to about 0.9 mm. Preferably the shaft diameter is in a range from about 0.6 mm to about 0.9 mm. Preferably the shaft diameter is in a range from about 0.7 mm to about 0.9 mm. Preferably the shaft diameter is in a range from about 0.75 mm to about 0.85 mm. Preferably the shaft diameter is about 0.8 mm.

Applicant has discovered that a piercing element having a shaft diameter greater than about 1 mm results in non-uniform release of dry particles from the activated capsule during multiple inhalations. For example, a greater release of dry particles occurs during the first two inhalations substantially depleting the capsule within four or five inhalations.

The piercing element has only a single cutting plane defining a cutting plane angle between the longitudinal axis of piercing element and the single cutting plane in a range from about 25 degrees and about 35 degrees. Preferably the cutting plane angle is in a range from about 28 degrees and about 32 degrees. Preferably the cutting plane angle is about 30 degrees. These preferred cutting plane angles have been found to require a force of about 5 Newtons or less to activate or pierce the capsule with the inhaler system described herein.

Applicant has discovered that a piercing element having a cutting plane angle greater than about 40 degrees results in a piercing or activation force of about 7 Newtons or greater. Consumers report that a piercing or activation force of about 7 Newtons or greater is an uncomfortably high force to apply to the inhaler article holder or inhaler system.

Applicant has also discovered that a piercing element having a cutting plane angle less than about 20 degrees results in a non-robust piercing element. Piercing element having a cutting plane angle less than about 20 degrees may not provide uniform or repeatable aperture formation in the capsule.

The piercing element cutting plane may define a pointed oval shape. One point of the pointed oval shape may define the tip of the piercing element. The opposing tip of the pointed oval shape may define the termination of the cutting plane with the intersection of the shaft circumference.

The piercing element longitudinal axis may be offset from the sleeve longitudinal axis or capsule cavity longitudinal axis by at least one piercing element diameter or at least one shaft diameter, or at least 1.5 piercing element diameters or at least 1.5 shaft diameters, or at least 2 piercing element diameters or at least 2 shaft diameters, or in a range from 1 to 2 piercing element diameters, or in a range from 1 to 2 shaft diameters.

The hemispherical endcap of the capsule has a radius of 0% at the central longitudinal axis of the capsule and a radius of 100% at the outer circumference of the hemispherical endcap of the capsule. The single offset piercing element may pierce the capsule hemispherical endcap in a range from 25% to 90% of a capsule radius away from the capsule longitudinal axis, or from 33% to 80% of the capsule radius away from the capsule longitudinal axis, or 50% to 75% of the capsule radius away from the capsule longitudinal axis.

The hemispherical endcap of the capsule may have an outer radius in a range from 2.6 mm to 3.2 mm or about 3 mm, or a diameter in a range from about 5.4 mm to about 6.4 mm, or about 6 mm. The piercing element may pierce the capsule at the capsule curved end or hemispherical endcap at a radial distance of at least 1 mm from the capsule longitudinal axis, or in a range from about 1 mm to about 2.5 mm from the capsule longitudinal axis or in a range from about 1.5 mm to about 2.2 mm from the capsule longitudinal axis, or at about 2 mm from the capsule longitudinal axis.

The piercing element tip has only a single bevel or cutting plane. This single bevel or cutting plane may be specifically oriented relative to the piercing element offset to achieve reliable and repeatable piercing without orientating or aligning the capsule relative to the piercing element.

The piercing element single bevel or cutting plane may define a planar surface opposing the sleeve longitudinal axis. The piercing element single bevel or cutting plane may define a planar surface opposing the capsule longitudinal axis. The piercing element single bevel or cutting plane defines a planar surface that may face a sleeve inner diameter surface closest to the planar surface. The piercing element single bevel may face toward the capsule. The piercing element single bevel may face away from the capsule.

The piercing element forms a single aperture in the capsule defining only a single hinge of capsule material extending into the capsule cavity. The single hinge of capsule material may be located at a point around the single aperture furthest from the capsule longitudinal axis.

The piercing element forms a single aperture in the capsule defining only a single hinge of capsule material extending into the capsule cavity. The hinge is formed when the beveled tip of the piercing element pierces the capsule. As the beveled tip of the piercing element enters the capsule, the beveled tip of the piercing element cuts the capsule to form an aperture. Then, as the beveled tip of the piercing element continues to enter the capsule, it continues to cut the capsule. The hinge is formed as the end of the bevel enters the capsule. When piercing element is then removed from the capsule, an aperture with a hinge is formed in the capsule. Thus, an aperture is formed in the capsule substantially related to the size of the piercing element, with the hinge formed in the aperture opposite the tip of the piercing element. If the piercing element single bevel faces toward the capsule, the hinge is formed at the inside edge of the aperture, where the inside edge is closer to the longitudinal axis of the capsule. If the piercing element single bevel faces away from the capsule, the hinge is formed at the outside edge of the aperture, where the outside edge is farther away from the longitudinal axis of the capsule. When the beveled tip of the piercing element faces away from the longitudinal axis of the capsule, a single hinge of capsule material is formed located at a point of the single aperture furthest from the capsule longitudinal axis.

The sleeve closed end may further include a sleeve bottom element substantially forming the closed end of the sleeve. The sleeve bottom element may be fixed and contact the airflow element. The sleeve bottom element may extend away from the airflow element a distance along the sleeve longitudinal axis and toward the closed end of the housing cavity. The sleeve bottom element may have an aperture that contains the piercing element and allows the piercing element to pass through the sleeve bottom element aperture.

The inhaler article holder may further include a spring member configured to bias the sleeve away from the piercing element. The spring member may bias the sleeve away from the second position to the first position. The spring member may be in a relaxed state in the sleeve first position. The spring member may be in a compressed state in the second position. Preferably the piercing element is disposed within the spring member.

The sleeve may include an elongated slot extending along a longitudinal length of the sleeve. The housing may further include a pin extending from an inner surface of the housing cavity. The pin may be configured to mate with the elongated slot to maintain alignment of the sleeve as it moved between the first and second positions.

An inner housing may be contained within the housing cavity. The inner housing may separate at least a portion of the sleeve from the inner surface of the housing cavity. The inner housing may separate a fixed end of the piercing element from the inner surface of the housing cavity. The inner housing may separate at the spring member from the inner surface of the housing cavity.

Inhalable powders may include various active agents. The active agent may comprise an alkaloid such as nicotine or anatabine or anabasine, for example. Preferably, the active agent comprises solid salt of an alkaloid, such as a nicotine salt.

The amount of active agent may be selected based on the desired or intended use of the inhalable dry powder. For example, the amount of active agent may be between 0.5 wt-% and 10 wt-% of the total weight of the dry powder particles. The dry powder particles may comprises 0.5 wt-% or more, 1 wt-% or more, 2 wt-% or more, or 3 wt-% or more of the active agent, and 12 wt-% or less, 10 wt-% or less, 9 wt-% or less, 8 wt-% or less, or 7 wt-% or less, of the active agent, or from 0.5 wt-% to 10 wt-%, from 1 wt-% to 8 wt-%, from 1.5 wt-% to 6 wt-%, or from 2 wt-% to wt-of the active agent.

The dry powder particles may comprises 0.5 wt-% or more, 1 wt-% or more, 2 wt-% or more, or 3 wt-% or more of nicotine, and 12 wt-% or less, 10 wt-% or less, 9 wt-% or less, 8 wt-% or less, or 7 wt-% or less, of nicotine, or from 0.5 wt-% to 10 wt-%, from 1 wt-% to 8 wt-%, from 1.5 wt-% to 6 wt-%, or from 2 wt-% to 5 wt-% nicotine.

The amount of active agent may also be selected on a per-dose basis. The inhalable powder may be packaged in a single dose form or in a multiple dose form. For example, the inhalable powder may comprise 0.5 mg or more, 1 mg or more, 2 mg or more, or 5 mg or more of the active agent per dose. The inhalable powder may comprise 500 mg or less, 200 mg or less, 100 mg or less, 50 mg or less, 20 mg or less, or 10 mg or less of the active agent per dose. In some embodiments, the inhalable powder comprises from 0.01 to 10 mg of anatabine or nicotine or anabasine per dose, 0.05 to 5 mg anatabine or nicotine or anabasine per dose, or 0.1 to 1 mg of anatabine or nicotine or anabasine per dose.

In embodiments, the capsule contains from 1 to 20 doses. In embodiments, the capsule contains from 1 to 10 doses. In embodiments the capsule contains from 10 to 20 doses. In embodiments, the capsule contains 1 dose. In embodiments, the capsule contains 2 doses. In embodiments, the capsule contains 3 doses. In embodiments, the capsule contains 4 doses. In embodiments, the capsule contains 5 doses. In embodiments, the capsule contains 6 doses. In embodiments, the capsule contains 7 doses. In embodiments, the capsule contains 8 doses. In embodiments, the capsule contains 9 doses. In embodiments, the capsule contains 10 doses. In embodiments, the capsule contains 11 doses. In embodiments, the capsule contains 12 doses. In embodiments, the capsule contains 13 doses. In embodiments, the capsule contains 14 doses. In embodiments, the capsule contains 15 doses. In embodiments, the capsule contains 16 doses. In embodiments, the capsule contains 17 doses. In embodiments, the capsule contains 18 doses. In embodiments, the capsule contains 19 doses. In embodiments, the capsule contains 20 doses.

The dry powder particles may have a particle size of 20 μm or less, 10 μm or less, or 5 μm or less, or 0.1 μm or greater, 0.2 μm or greater, or 0.5 μm or greater, or ranging from 0.5 μm to 10 μm, or from 0.75 μm to 5 μm, or from 1 μm to 5 μm, or from 1 μm to 3 μm, or from 1.5 μm to 2.5 μm. The desired particle size range may be achieved by spray drying, milling, sieving, or a combination thereof.

The dry powder particles may be further mixed with a second population of particles to form a powder system. Preferably, the second population of particles have a different particle size or larger particle size than the dry powder particles. For example, the second population of particles may have a particle size of about 20 μm or greater, or about 50 μm or greater, 200 μm or smaller, 150 μm or smaller, or in a range from 50 μm to 200 μm, or from 50 μm to 150 μm. The second population of particles may have any useful size distribution for inhalation delivery selectively into the mouth or buccal cavity of a user. The larger second population of flavourant particles may assist in delivery of the dry powder particles to the inhalation airflow to the user.

The dry powder particles and second population of particles may be combined in any useful relative amount so that the second population of particles are detected by the user when consumed with the dry powder particles. Preferably, the dry powder particles and second population of particles form at least about 90 wt-% or at least about 95 wt-% or at least about 99 wt-% or 100 wt-% of the total weight of the powder system.

The dry powder particles may be mixed with a second population of flavourant particles to form a powder system. Preferably, the second population of flavourant particles have a different particle size or larger particle size than the dry powder particles. For example, the flavor particles may have a particle size of about 20 μm or greater, or about 50 μm or greater, 200 μm or smaller, 150 μm or smaller, or in a range from 50 μm to 200 μm, or from 50 μm to 150 μm. The second population of flavourant particles may have any useful size distribution for inhalation delivery selectively into the mouth or buccal cavity of a user. The larger second population of flavourant particles may assist in delivery of the dry powder particles to the inhalation airflow to the user.

The dry powder particles and second population of flavourant particles may be combined in any useful relative amount so that the second population of flavourant particles are detected by the user when consumed with the dry powder particles. Preferably, the dry powder particles and second population of flavourant particles form at least about 90 wt-% or at least about 95 wt-% or at least about 99 wt-% or 100 wt-% of the total weight of the powder system.

The dry powder particles or powder system may be provided in a suitable dosage form. For example, the dry powder particles or powder system may be provided in a capsule. The dosage form (for example, capsule) may be configured for use in a suitable inhaler. For example, the capsule may be utilized in an inhaler device having a capsule cavity. Air flow management through a capsule cavity of the inhaler device may cause a capsule contained therein to rotate during inhalation and consumption. The capsule may contain dry powder particles or powder system.

The term "particle size" is used here to refer to the mass median aerodynamic diameter (MMAD) of the particle or set of particles, unless otherwise stated. Such values are based on the distribution of the aerodynamic particle diameters defined as the diameter of a sphere with a density of 1 gm/cm 3 that has the same aerodynamic behavior as the particle which is being characterized.

In particular, for a powder system reference is commonly made to the mass median aerodynamic diameter (MMAD), one of the metrics most widely adopted as a single number descriptor of aerodynamic particle-size distribution. The MMAD is a statistically derived figure for a particle sample: by way of example, an MMAD of 5 micrometres means that 50 percent of the total sample mass will be present in particles having aerodynamic diameters of less than 5 micrometres, and that the remaining 50 percent of the total sample mass will be present in particles having an aerodynamic diameter greater than 5 micrometres. In the context of the present invention, when describing a powder system, the term "particle size" preferably refers to the MMAD of the powder system.

The MMAD of a powder system is preferably measured with a cascade impactor. Cascade impactors are instruments which have been extensively used for sampling and separating airborne particles for determining the aerodynamic size classification of aerosol particles. In practice, cascade impactors separate an incoming sample into discrete fractions on the basis of particle inertia, which is a function of particle size, density and velocity. A cascade impactor typically comprises a series of stages, each of which comprises a plate with a specific nozzle arrangement and a collection surface. As nozzle size and total nozzle area both decrease with increasing stage number, the velocity of the sample-laden air increases as it proceeds through the instrument. At each stage, particles with sufficient inertia break free from the prevailing air stream to impact on the collection surface. Therefore, at any given flow rate, each stage is associated with a cut-off diameter, a figure that defines the size of particles collected. With increasing stage number, velocity increases and so stage cut-off diameter decreases. Thus, the cut-off diameter associated with a given stage is a function of the air-flow rate used for testing. To reflect in-use performance, nebulisers are routinely tested at 15 L/min and dry powder inhalers may be tested at flow rates up to 100 L/min.

Preferably, in the context of the present invention, the MMAD of a powder system is measured with a Next Generation Impactor (NGI) 170 (available from Copley Scientific AG). The NGI is a high performance, precision, particle classifying cascade impactor having seven stages plus a Micro-Orifice Collector (MOC). Characteristics and operation principle of a NGI are described, for example, in Marple et al., Journal of Aerosol Medicine—Volume 16, Number 3 (2003). More preferably, measurements are carried out at 20±3 degrees Celsius and relative humidity of 35±5 percent.

A dry powder formulation typically contains less than or equal to about 15 percent by weight moisture, preferably less than or equal to about 10 percent moisture, even more preferably less than or equal to about 6 percent by weight moisture. Most preferably a dry powder formulation contains less than or equal to about 5 percent by weight moisture or even less than or equal to about 3 percent by weight moisture or even less than or equal to about 1 percent by weight moisture.

All values reported as a percentage are presumed to be weight percent based on the total weight.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

The term "substantially" as used here has the same meaning as "significantly," and can be understood to modify the relevant term by at least about 90%, at least about 95%, or at least about 98%. The term "not substantially" as used here has the same meaning as "not significantly," and can be understood to have the inverse meaning of "substantially," i.e., modifying the relevant term by not more than 10%, not more than 5%, or not more than 2%.

The invention is defined in the claims. However, below there is provided a non-exhaustive listing of non-limiting examples. Any one or more of the features of these examples may be combined with any one or more features of another example, embodiment, or aspect described herein.

Example Ex1. An inhaler system comprising a housing defining a housing cavity, a sleeve extending along a sleeve longitudinal axis and positioned within the housing cavity, a capsule is contained within the sleeve and has a capsule longitudinal axis, and a piercing element comprising only a single shaft extends from a fixed end to a tip along a piercing element longitudinal axis. The piercing element longitudinal axis is parallel with the sleeve longitudinal axis. The piercing element has a piercing element diameter in a range from 0.5 to 0.9 mm. The single piercing element tip has only a single cutting plane and defining a cutting plane angle between the longitudinal axis of the piercing element and the single cutting plane. The cutting plane angle is in a range from about 25 degrees and about 35 degrees. The sleeve is movable within the housing cavity between a first position and a second position. Only a single aperture is formed in the capsule when the sleeve is moved from the first position to the second position.

Example Ex2. An inhaler system comprising a housing defining a housing cavity, a sleeve extending along a sleeve longitudinal axis and positioned within the housing cavity. The sleeve is movable within the housing cavity between a first position and a second position. The sleeve extends from an open end to a closed end and defines a cylindrical lumen for receiving an inhaler article. The open end of the sleeve is aligned with an opening in the housing for receiving the inhaler article. A capsule is contained within the inhaler article and received within the sleeve. The capsule has a capsule longitudinal axis. A piercing element comprises only a single shaft extending from a fixed end to a tip along a piercing element longitudinal axis. The piercing element longitudinal axis is parallel with the sleeve longitudinal axis. The piercing element has a piercing element diameter in a range from 0.5 to 0.9 mm, and the single piercing element tip having only a single cutting plane and defining a cutting plane angle between the longitudinal axis of the piercing element and the single cutting plane. The cutting plane angle being in a range from about 25 degrees and about 35 degrees. Only a single aperture is formed in the capsule when the sleeve is moved from the first position to the second position.

Example Ex3. The inhaler system of Ex1 or Ex2, wherein the piercing element diameter is a range from 0.7 to 0.9 mm.

Example Ex4. The inhaler system of any preceding Example, wherein the cutting plane angle is in a range from about 28 degrees and about 32 degrees.

Example Ex5. The inhaler system of any preceding Example, wherein the piercing element diameter is about 0.8 mm.

Example Ex6. The inhaler system of any preceding Example, wherein the cutting plane angle is about 30 degrees.

Example Ex7. The inhaler system of any preceding Example, wherein the piercing element cutting plane defines a pointed oval shape.

Example Ex8. The inhaler system of any preceding Example, wherein the piercing element comprises a single solid cylindrical shaft extending from the fixed end to a tip along the piercing element longitudinal axis.

Example Ex9. The inhaler system of any preceding Example, wherein the capsule has a diameter in a range from about 5.2 to 6.4 mm.

Example Ex10. The inhaler system of any preceding Example, wherein the piercing element forms a single aperture in the capsule defining only a single hinge of capsule material extending into the capsule cavity.

Example Ex11. The inhaler system of any preceding Example, wherein a force required for the piercing element to pierce the capsule is about 5 N or less.

Example Ex12. The inhaler system of any preceding Example, wherein the piercing element longitudinal axis is offset from the sleeve longitudinal axis.

Example Ex13. The inhaler system of any preceding Example, wherein the piercing element pierces the capsule at a capsule curved end in a range from 25% to 90% of a capsule radius away from the capsule longitudinal axis, or from 33% to 80% of the capsule radius away from the capsule longitudinal axis, or 50% to 75% of the capsule radius away from the capsule longitudinal axis.

Example Ex14. The inhaler system of any preceding Example, wherein the sleeve extends from an open end to a closed end and defines a cylindrical lumen for receiving an inhaler article, the open end of the sleeve is aligned with an opening in the housing for receiving an inhaler article, the closed end of the sleeve comprises an airflow element configured to form swirling airflow to spin the capsule about the capsule longitudinal axis during use.

Example Ex15. The inhaler system of any preceding Example, wherein the capsule is contained within an inhaler article extending along an inhaler article longitudinal axis from a distal end to a mouthpiece end, the sleeve is configured to receive the distal end of the inhaler article and transmit swirling or rotational inhalation airflow into the distal end of the inhaler article.

Example Ex16. The inhaler system of any preceding Example, wherein the housing cavity comprises a spring member to bias the capsule away from the piercing element.

Example Ex17. The inhaler system of any preceding Example, wherein the capsule contains pharmaceutically active particles comprising nicotine, the pharmaceutically active particles having a mass median aerodynamic diameter of about 5 micrometres or less, or in a range from about 0.5 micrometres to about 4 micrometres, or in a range from about 1 micrometres to about 3 micrometres.

Example Ex18. The inhaler system of any preceding Example, wherein the capsule further contains flavour particles having a mass median aerodynamic diameter of about 20 micrometres or greater, or about 50 micrometres or greater, or in a range from about 50 to about 200 micrometres, or from about 50 to about 150 micrometres.

Example Ex19. An inhaler system includers a housing defining a housing cavity, a sleeve extending along a sleeve longitudinal axis and positioned within the housing cavity, a capsule is contained within the sleeve and has a capsule longitudinal axis, and a piercing element comprising only a single shaft extends from a fixed end to a tip along a piercing element longitudinal axis. The piercing element longitudinal axis is parallel with and offset from the sleeve longitudinal axis. The piercing element has a piercing element diameter in a range from 0.5 to 0.9 mm. The single piercing element tip has only a single cutting plane and defining a cutting plane angle between the longitudinal axis of the piercing element and the single cutting plane. The cutting plane angle is in a range from about 25 degrees and about 35 degrees.

The sleeve is movable within the housing cavity between a first position and a second position. Only a single aperture is formed in the capsule when the sleeve is moved from the first position to the second position.

Example Ex20. The inhaler system of Ex19, wherein the piercing element longitudinal axis is offset from the sleeve longitudinal axis by at least one piercing element diameter, or at least 1.5 piercing element diameters, or at least 2 piercing element diameters, or in a range from 1 to 2 piercing element diameters.

Example Ex21. The inhaler system of any preceding Example, wherein the inhaler system has less than two piercing elements.

Example Ex22. The inhaler system of any preceding Example, wherein the piercing element single bevel or cutting plane defines a planar surface opposing the sleeve longitudinal axis.

Example Ex23. The inhaler system of any preceding Example, wherein the piercing element single bevel or cutting plane defines a planar surface opposing the capsule longitudinal axis.

Example Ex24. The inhaler system of any preceding Example, wherein the piercing element single bevel or cutting plane defines a planar surface facing a sleeve inner diameter surface closest to the planar surface.

Example Ex25. The inhaler system of any of Ex19 to Ex24, wherein the piercing element pierces the capsule at the capsule curved end in a range from 25% to 80% of a capsule radius away from the capsule longitudinal axis, or from 33% to 75% of the capsule radius away from the capsule longitudinal axis, or 50% to 75% of the capsule radius away from the capsule longitudinal axis.

Example Ex26. The inhaler system of any of Ex19 to Ex25, wherein the piercing element forms a single aperture in the capsule defining only a single hinge of capsule material extending into the capsule cavity.

Example Ex27. The inhaler system of any of Ex19 to Ex26, wherein the single hinge of capsule material is located at a point around the single aperture furthest from the capsule longitudinal axis.

Example Ex28. The inhaler system of any of Ex19 to Ex27, the piercing element comprises a single solid shaft extending from the fixed end to a tip along the piercing element longitudinal axis.

Example Ex29. The inhaler system of any of Ex19 to Ex28, wherein the capsule has a radius in a range from 2.6 mm to 3.2 mm and the piercing element pierces the capsule at the capsule curved end in a radial distance of at least 1 mm from the capsule longitudinal axis, or in a range from about 1 mm to about 2 mm from the capsule longitudinal axis.

Example Ex30. The inhaler system of any of Ex19 to Ex 29, wherein the sleeve extends from an open end to a closed end and defines a cylindrical lumen for receiving an inhaler article, the open end of the sleeve is aligned with an opening in the housing for receiving an inhaler article, the closed end of the sleeve comprises an airflow element configured to form swirling airflow to spin the capsule about the capsule longitudinal axis during use.

Example Ex31. The inhaler system of any of Ex19 to Ex 30, wherein the capsule is contained within an inhaler article, the inhaler article extends along an inhaler article longitudinal axis from a distal end to a mouthpiece end, the sleeve is configured to receive the distal end of the inhaler article.

Example Ex32. The inhaler system of Ex31, wherein the inhaler article longitudinal axis is offset from the piercing element longitudinal axis.

Example Ex33. The inhaler system of any of Ex19 to Ex 32, wherein the capsule contains pharmaceutically active particles comprising nicotine, the pharmaceutically active particles having a mass median aerodynamic diameter of about 5 micrometres or less, or in a range from about micrometres to about 4 micrometres, or in a range from about 1 micrometres to about 3 micrometres.

Example Ex34. The inhaler system of Ex33, wherein the capsule further contains flavour particles having a mass median aerodynamic diameter of about 20 micrometres or greater, or about 50 micrometres or greater, or in a range from about 50 to about 200 micrometres, or from about 50 to about 150 micrometres.

The Examples will now be further described with reference to the figures in which.

Figure 5:
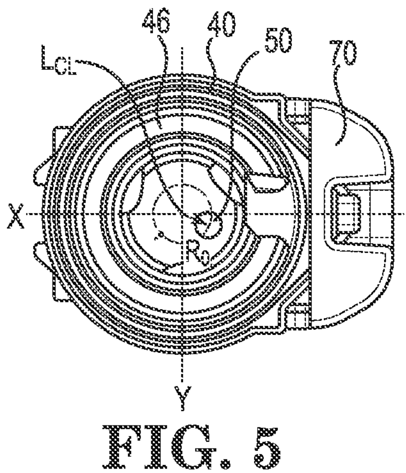
Figure 6A:
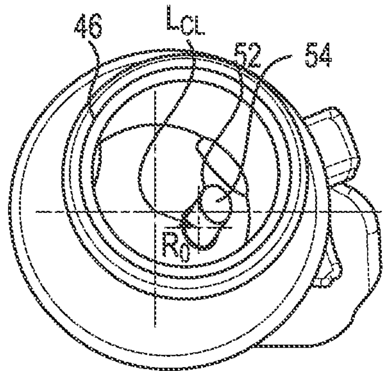
Figure 7:
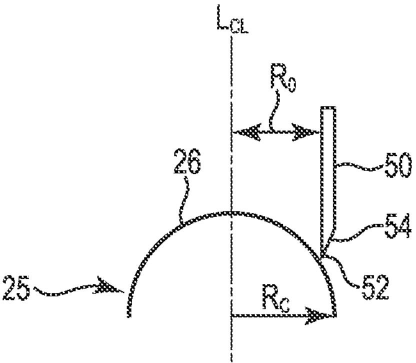
Figure 6B:
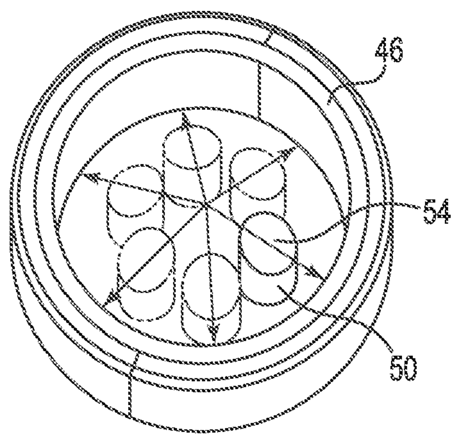
Figure 8:
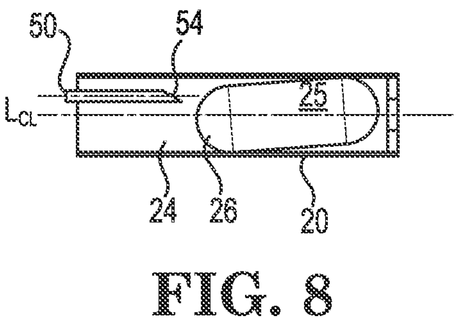

FIG. 5 a front elevation into the sleeve of an illustrative inhaler article holder;

FIG. 6A is a perspective view of an illustrative airflow element with piercing element;

FIG. 6B is a perspective view of an airflow element illustrating six alternative piercing element offset locations about the centerline of the airflow element;

FIG. 7 is a schematic cross-sectional diagram of an illustrative piercing element contacting a capsule endcap;

FIG. 8 is a schematic cross-sectional diagram of an illustrative capsule cavity with a capsule and piercing element.

Figure 9A:
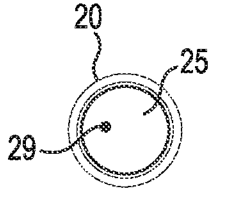
Figure 9A:
Figure 9B:
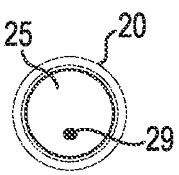
Figure 10:
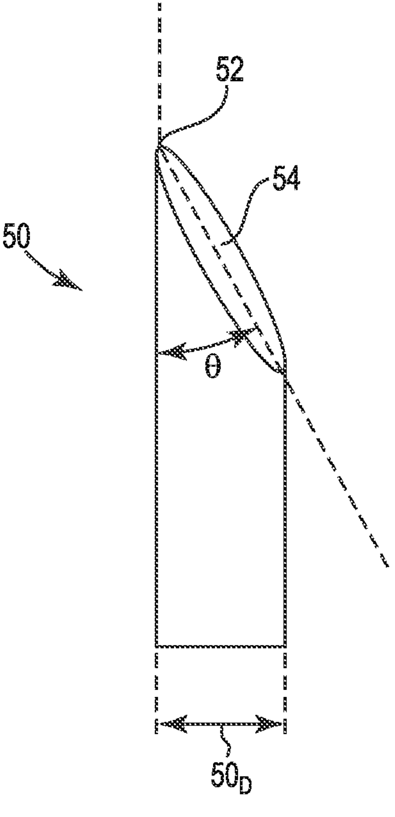

FIG. 9A is a front elevation view of an illustrative capsule endcap after being pierced by the piercing element described herein;

FIG. 9B is a front elevation view of another illustrative capsule endcap after being pierced by the piercing element described herein;

FIG. 10 is a perspective view of an illustrative piercing element tip.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 1:
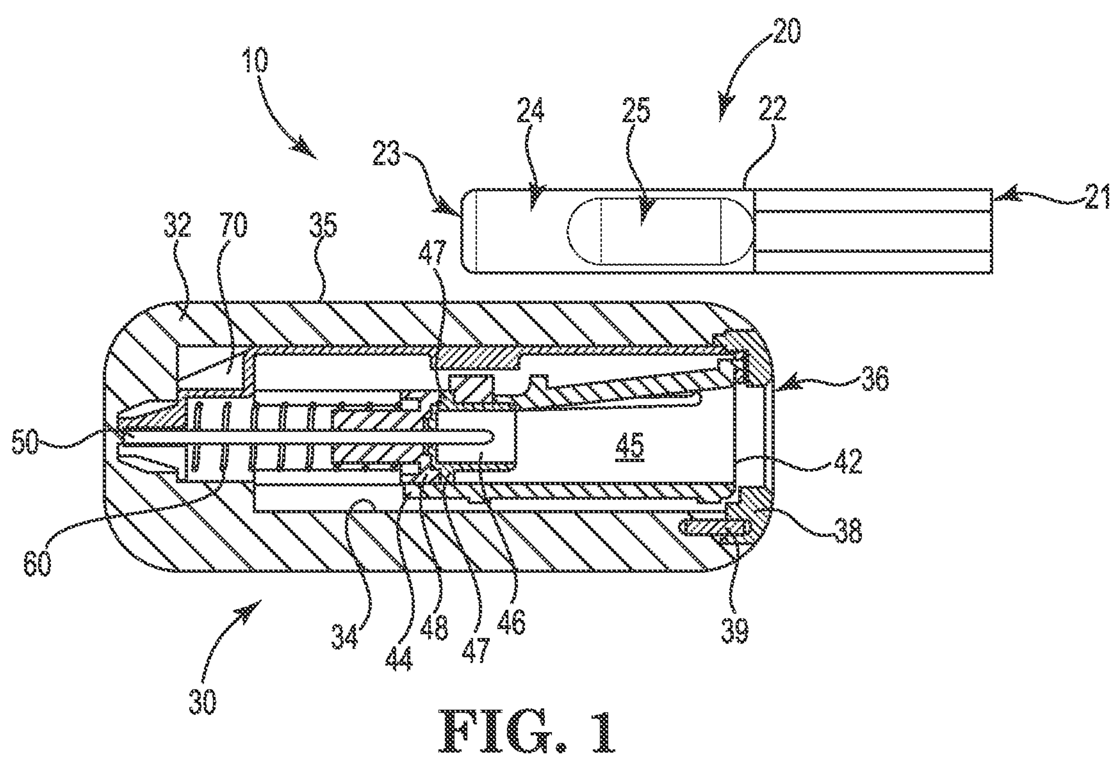
FIG. 1 is a schematic cross-sectional diagram of an illustrative inhaler system.
Figure 2:
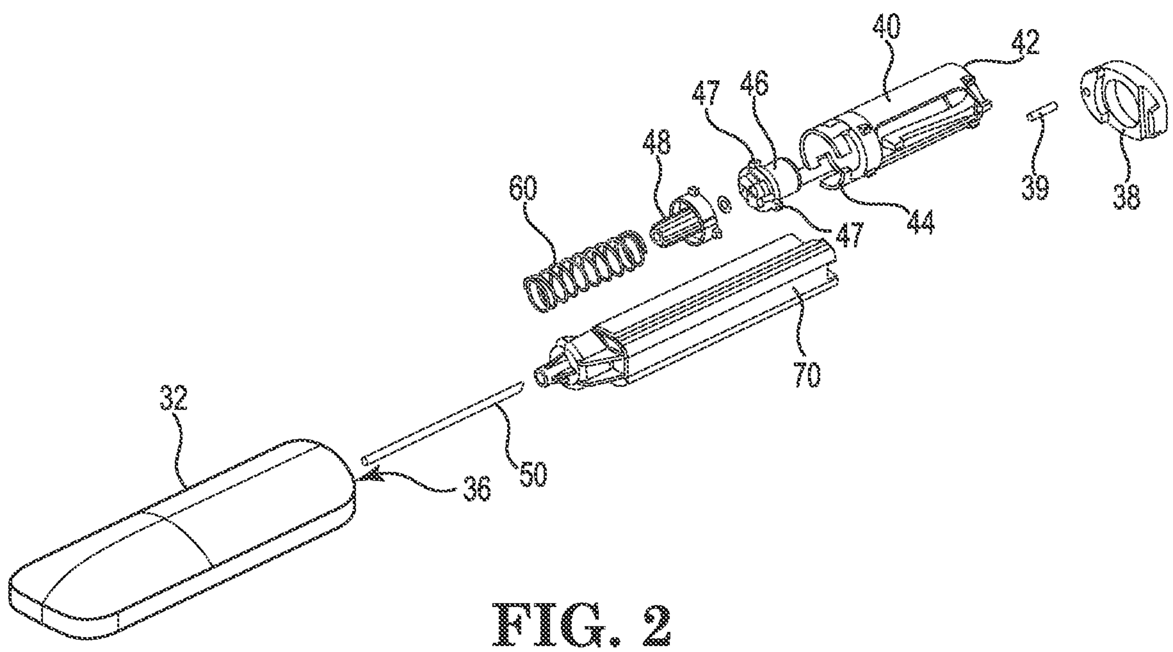
FIG. 2 is perspective exploded view of an illustrative inhaler article holder.
Figure 3A:
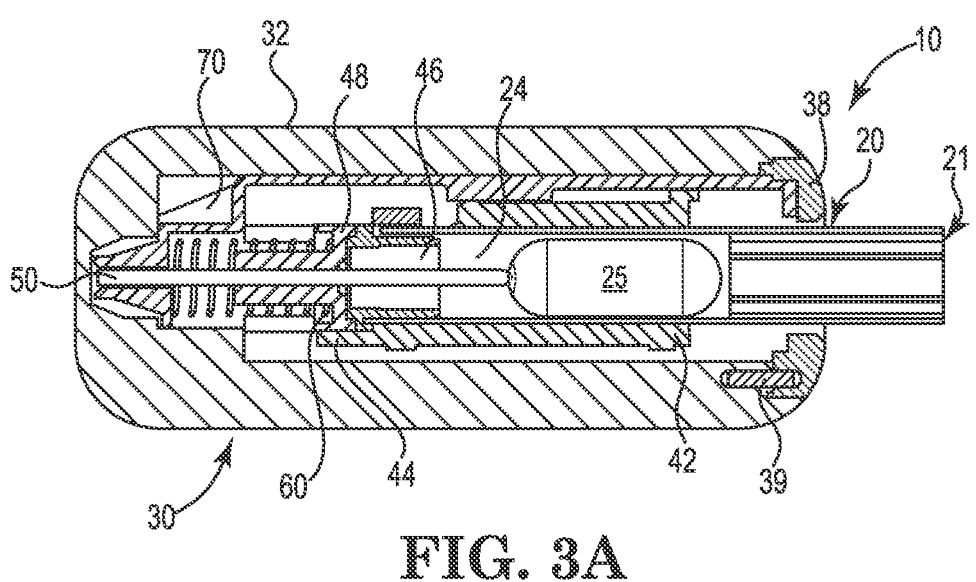
FIG. 3A is a schematic cross-sectional diagram of an illustrative inhaler system where the inhaler article is received in the inhaler article holder and piercing the capsule in a second position.
Figure 3B:
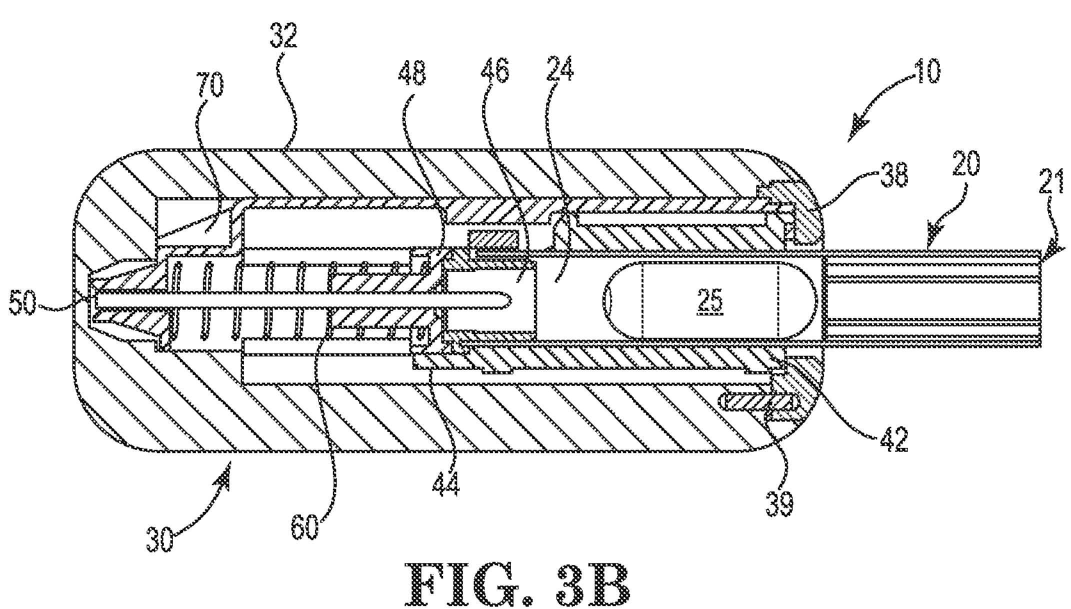
FIG. 3B is a schematic cross-sectional diagram of the illustrative inhaler system of FIG. 3A where the piercing element is retracted from the capsule in a first position.
Figure 4:
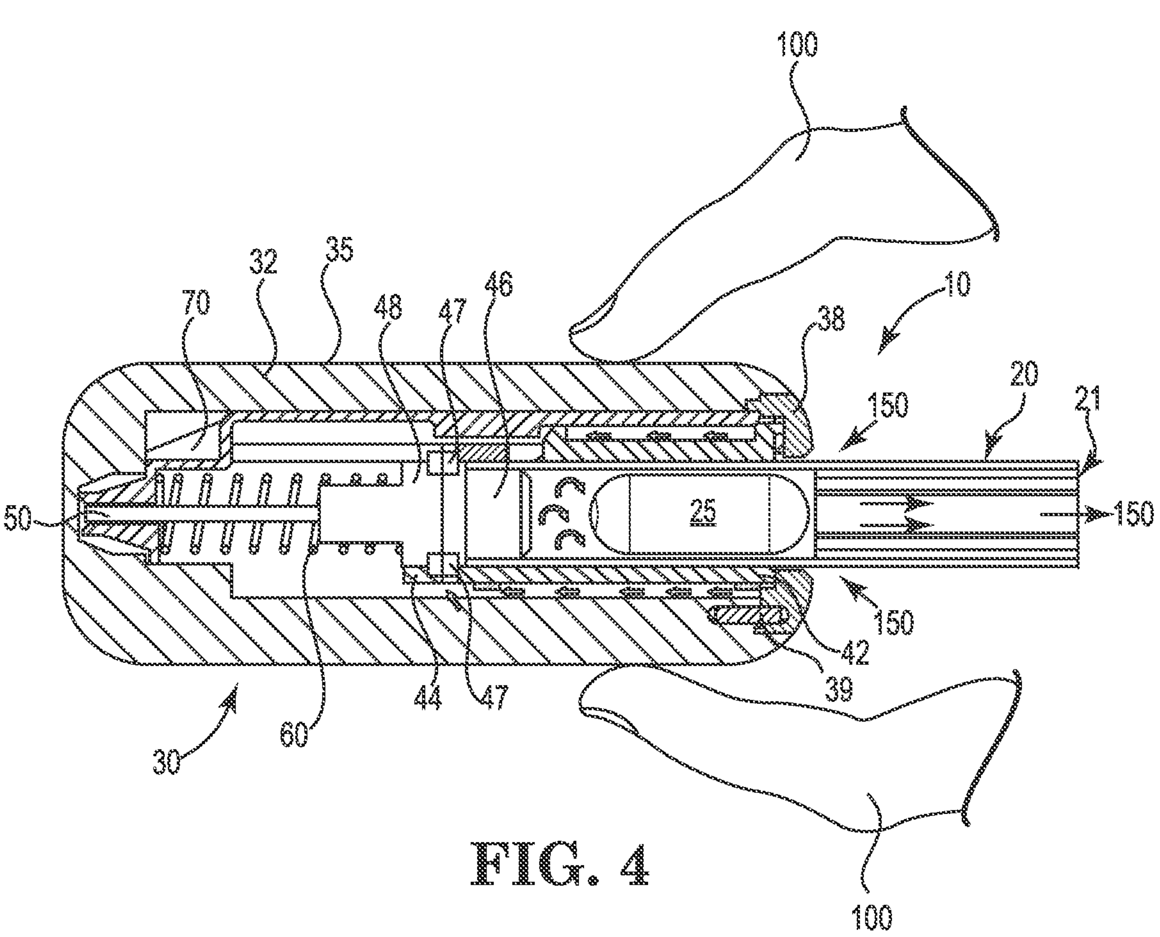
FIG. 4 is another schematic cross-sectional diagram of FIG. 3B illustrating the inhalation airflow path through the inhaler system.

FIG. 1 is a schematic cross-sectional diagram of an illustrative inhaler system 10. FIG. 2 is perspective exploded view of an illustrative inhaler article holder 30. FIG. 3A is a schematic cross-sectional diagram of an illustrative inhaler system 10 where the inhaler article 20 is received in the inhaler article holder 30 and piercing the capsule 25 (contained within the inhaler article 20) in a second or compressed position. FIG. 3B is a schematic cross-sectional diagram of the illustrative inhaler system 10 of FIG. 3A where the piercing element 50 is retracted from the capsule 25 in a first or relaxed position. FIG. 4 is another schematic cross-sectional diagram of FIG. 3B illustrating the inhalation airflow 150 path (arrows) through the inhaler system 10.

The inhaler article holder 30 is configured to receive a separate consumable inhaler article 20 and induce swirling inhalation airflow into and through an inhaler article 20 during consumption. The inhaler article holder 30 and an inhaler article 20 form an inhaler system 10. The inhaler article 20 remains in the inhaler article holder 30 during use by the consumer. The inhaler article holder 30 is configured to induce swirling inhalation airflow entering the received inhaler article 20.

The illustrative inhaler article 20 includes a body 22 extending from a mouthpiece end 21 to a distal end 23. A capsule cavity 24 is defined within the body 22. A capsule 25 is contained within the capsule cavity 24. Dry powder particles described above may be contained within the capsule 25. The capsule 25 may be pierced to form an aperture through the body of the capsule 25 and inhalation air may flow through the inhaler article 20 to release dry powder particles from the pierced capsule 25 and into the inhalation airflow and out of the mouthpiece end 21.

The inhaler article holder 30 includes a housing 32 defining a housing cavity defined by a housing inner surface 34, and an outer surface 35. A sleeve 40 is positioned within the housing cavity. The sleeve 40 is arranged to receive an inhaler article 20 and the sleeve 40 is movable within the housing cavity between a first position and a second position, along a longitudinal axis of the housing cavity.

A piercing element 50 is arranged to pierce the capsule 25 within the inhaler article 20 received within the sleeve 40 when the sleeve 40 is in the second position as illustrated in FIG. 3A.

The piercing element 50 may be configured to extend into the sleeve 40 along a longitudinal axis of the housing 32. The inhaler article holder 30 may include a spring member 60 configured to bias the sleeve 40 and any received inhaler article 20 away from the piercing element 50.

The sleeve 40 extends from an open end 42 to a closed end 44 (or restricted end) and defines a sleeve cavity 45 or cylindrical lumen 45 along a longitudinal axis of the sleeve 40. The open end 42 of the sleeve aligns with the single housing opening 36.

The sleeve closed end 44 includes an airflow element 46 and an aperture to allow the piercing element to pass through the closed end 44 and extend into the sleeve lumen 45. The airflow element 46 includes one or more inhalation air inlets 47 that provide airflow communication from the annular space around the sleeve 40 into the sleeve cylindrical lumen 45. This airflow element 46 is configured to induce rotating or swirling inhalation airflow into the sleeve cylindrical lumen 45 and directly into the inhaler article capsule cavity 24. This swirling or rotational inhalation airflow may be transmitted into an inhaler article 20 to rotate a capsule 25 and release dry powder contained within the capsule 25.

The airflow element 46 of the sleeve 40 includes a tubular element having a central passage in fluid communication with the sleeve cavity 45. The airflow element 46 has at least one air inlet 47 allowing inhalation air 150 to enter into the central passage. The at least one air inlet 47 extends in a direction that is tangential to the central passage to generate the swirling or rotational inhalation airflow.

The sleeve 40 includes a tubular element that may extend into the sleeve cavity 45 about mm and have an outer diameter of about 5.5 mm and an inner diameter of about 4 mm. The received inhaler article 20 open distal end 23 may have an inner diameter of about 5.5 mm to provide an interference fit with the airflow element 46 tubular element.

The sleeve closed end 44 may further include a sleeve bottom element 48 substantially forming the closed end of the sleeve 40. The sleeve bottom element 48 may be fixed and contact the airflow element 46. The sleeve bottom element 48 may extend away from the airflow element 46 a distance along the sleeve longitudinal axis and toward the closed end of the housing cavity. The sleeve bottom element 48 may have an aperture that contains the piercing element 50 and allows the piercing element 50 to pass through the sleeve bottom element 48 aperture.

An inner housing 70 may be contained within the housing cavity. The inner housing 70 may separate at least a portion of the sleeve 40 from the inner surface of the housing cavity. The inner housing 70 may separate a fixed end of the piercing element 50 from the inner surface of the housing cavity. The inner housing 70 may separate the spring member 60 from the inner surface of the housing cavity.

An annular cover 38 may secure the inner housing 70 and sleeve 40 into the housing cavity. The annular cover 38 defines the single housing opening 36 for receiving the inhaler article 20. The annular cover 38 may be fixed to the housing 32 with a pin element 39.

FIG. 4 illustrates the inhalation airflow 150 path through the inhaler system 10. Inhalation airflow 150 enters the inhaler article holder 30 along the outer surface of the received inhaler article 20 and the annular cover 38. Once inside the housing cavity, the inhalation air 150 travels along the sleeve 40 length to the closed end 44 of the sleeve 40. The inhalation air 150 then enters the air inlet 47 of the airflow element 46 and forms swirling or rotating inhalation air 150 within the sleeve lumen 45. This swirling or rotating inhalation air is then directly transmitted into the distal end 23 of the inhaler article 20 and into the capsule cavity 24. The swirling inhalation airflow rotates or agitates the capsule 25 and dry powder particles are entrained in the inhalation airflow. The entrained inhalation airflow then flows out of the inhaler article via the mouthpiece end 21 and to the user 100. The inhalation airflow 150 path is illustrated in FIG. 4 with arrows.

FIG. 5 a front elevation into the sleeve 40 of an illustrative inhaler article holder. FIG. 6A is a perspective view of an illustrative airflow element 46 with piercing element 50. FIG. 6B is a perspective view of an airflow element 46 illustrating six alternative piercing element 50 offset locations about the centerline of the airflow element 46.

The single cutting plane or bevel 54 is offset from or spaced away from and opposes or faces away from the centerline of the airflow element 46. FIG. 6B illustrates solid line embodiment and five phantom line alternative piercing element 50 offset locations about the centerline of the airflow element 46. Each alternative location illustrates that the single cutting plane or bevel 54 is offset from or spaced away from and opposes or faces away from the centerline of the airflow element 46.

The central longitudinal axis $L_{CL}$ of the sleeve 40 is located at the intersection of the X and Y axis. The airflow element 46 defines the closed end of the sleeve 40. An inner housing 70 is fixed to the sleeve 40. The piercing element 50 extends through the airflow element 46 and is offset from the central longitudinal axis $L_{CL}$ a distance $R_O$. The central longitudinal axis $L_{CL}$ of the airflow element 46 is aligned with and co-incident with the central longitudinal axis $L_{CL}$ of the sleeve 40. The cutting end of the piercing element is defined by a single cutting plane or bevel 54 terminating at a tip 52.

FIG. 7 is a schematic cross-sectional diagram of an illustrative piercing element 50 contacting a capsule endcap 26. FIG. 8 is a schematic cross-sectional diagram of an illustrative capsule cavity 24 of an inhaler article 20 with a capsule 25 and piercing element 50.

The orientation of the cutting plane or bevel 54 is illustrated in FIG. 7. The cutting place opposes the central longitudinal axis $L_{CL}$ of the sleeve 40. The central longitudinal axis $L_{CL}$ of the capsule cavity 24 aligned with and co-incident with the central longitudinal axis $L_{CL}$ of the sleeve 40. The tip 52 first penetrates the capsule hemispherical endcap 26 to form the aperture opening and continues to cut the capsule hemispherical endcap 26 until the entire circumference of the piercing element shaft enters the capsule 25. The portion of the perimeter forming the aperture is closest to the central longitudinal axis $L_{CL}$. A hinge of capsule material forming a portion of the aperture opposes the portion of the perimeter closest to the central longitudinal axis $L_{CL}$.

The piercing element 50 is parallel with and offset from the central longitudinal axis $L_{CL}$ a distance $R_O$. The capsule hemispherical endcap 26 has a radius $R_C$ at the circumference of the capsule 25. The piercing element 50 may contact the capsule hemispherical endcap 26 at a point closer to the circumference radius $R_C$ than the central longitudinal axis $L_{CL}$ as described above.

FIG. 9A is front elevation view of an illustrative capsule 25 endcap with aperture 29 after being pierced by the piercing element described herein. FIG. 9B is front elevation view of another illustrative capsule 25 endcap with aperture 29 after being pierced by the piercing element described herein.

FIG. 10 is a perspective view of an illustrative piercing element 50 tip 52. The piercing element 50 has only a single shaft extending from a fixed end to a tip 52 along a piercing element longitudinal axis. The piercing element has a piercing element diameter D in a range from 0.5 to mm, and the single piercing element tip 52 having only a single cutting plane 54 and defining a cutting plane angle Θ between the longitudinal axis of the piercing element and the single cutting plane 54. The cutting plane angle Θ being in a range from about 25 degrees and about 35 degrees.

For the purpose of the present description and of the appended claims, except where otherwise indicated, all numbers expressing amounts, quantities, percentages, and so forth, are to be understood as being modified in all instances by the term "about." Also, all ranges include the maximum and minimum points disclosed and include any intermediate ranges therein, which may or may not be specifically enumerated herein. In this context, therefore, a number A is understood as A±2% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

The invention claimed is:

1. An inhaler system, comprising:

a housing defining a housing cavity;

a sleeve extending along a sleeve longitudinal axis and positioned within the housing cavity, wherein the sleeve is movable within the housing cavity between a first position and a second position, wherein the sleeve extends from an open end to a closed end and defines a cylindrical lumen for receiving an inhaler article, the open end of the sleeve is aligned with an opening in the housing for receiving the inhaler article;

a capsule contained within the inhaler article and received within the sleeve, the capsule having a capsule longitudinal axis; and a piercing element comprising only a single shaft extending from a fixed end to a tip along a piercing element longitudinal axis, the piercing element longitudinal axis being parallel with the sleeve longitudinal axis, the piercing element having a piercing element diameter in a range from 0.5 to 0.9 mm, and the single piercing element tip having only a single cutting plane and defining a cutting plane angle between the longitudinal axis of the piercing element and the single cutting plane, the cutting plane angle being in a range from about 25 degrees and about 35 degrees, wherein the piercing element longitudinal axis is offset from the sleeve longitudinal axis;

wherein only a single aperture is formed in the capsule when the sleeve is moved from the first position to the second position.

2. The inhaler system according to claim 1, wherein the piercing element diameter is a range from 0.7 to 0.9 mm and the cutting plane angle is in a range from about 28 degrees and about 32 degrees.

3. The inhaler system according to claim 1, wherein the piercing element cutting plane defines a pointed oval shape.

4. The inhaler system according to claim 3, wherein the piercing element pierces the capsule at a capsule curved end in a range from 33% to 80% of a capsule radius away from the capsule longitudinal axis.

5. The inhaler system according to claim 3, wherein the piercing element diameter is about 0.8 mm and the cutting plane angle is about 30 degrees.

6. The inhaler system according to claim 3, wherein the piercing element pierces the capsule at a capsule curved end in a range from 50% to 75% of a capsule radius away from the capsule longitudinal axis, and the piercing element diameter is a range from 0.7 to 0.9 mm and the cutting plane angle is in a range from about 28 degrees and about 32 degrees.

7. The inhaler system according to claim 1, wherein the piercing element comprises a single solid cylindrical shaft extending from the fixed end to a tip along the piercing element longitudinal axis.

8. The inhaler system according to claim 1, wherein the capsule has a diameter in a range from about 5.2 to 6.4 mm.

9. The inhaler system according to claim 1, wherein the piercing element forms the single aperture in the capsule defining only a single hinge of capsule material extending into a capsule cavity.

10. The inhaler system according to claim 1, wherein a force required for the piercing element to pierce the capsule is about 5 N or less.

11. The inhaler system according to claim 1, wherein the piercing element pierces the capsule at a capsule curved end in a range from 25% to 90% of a capsule radius away from the capsule longitudinal axis.

12. The inhaler system according to claim 1, wherein the closed end of the sleeve comprises an airflow element configured to form swirling airflow to spin the capsule about the capsule longitudinal axis during use.

13. The inhaler system according to claim 1, wherein the capsule is contained within the inhaler article extending along an inhaler article longitudinal axis from a distal end to a mouthpiece end, the sleeve is configured to receive the distal end of the inhaler article and transmit swirling or rotational inhalation airflow into the distal end of the inhaler article.

14. The inhaler system according to claim 1, wherein the housing cavity comprises a spring member to bias the capsule away from the piercing element.

15. The inhaler system according to claim 1, wherein the capsule contains pharmaceutically active particles comprising nicotine, the pharmaceutically active particles having a mass median aerodynamic diameter of about 5 micrometres or less.

16. The inhaler system according to claim 15, wherein the capsule further contains flavour particles having a mass median aerodynamic diameter of about 2 about 50 micrometres or greater.

17. The inhaler system according to claim 15, wherein the capsule further contains flavour particles having a mass median aerodynamic diameter from about 50 to about 150 micrometres.

18. The inhaler system according to claim 1, wherein the piercing element pierces the capsule at a capsule curved end in a range from 50% to 75% of a capsule radius away from the capsule longitudinal axis.

19. The inhaler system according to claim 1, wherein the capsule contains pharmaceutically active particles comprising nicotine, the pharmaceutically active particles having a mass median aerodynamic diameter in a range from about 1 micrometre to about 3 micrometres.

* * * * *